United States Patent
Nakagawa et al.

(10) Patent No.: US 6,478,745 B2
(45) Date of Patent: Nov. 12, 2002

(54) INFLATABLE CUFF USED FOR BLOOD PRESSURE MEASUREMENT

(75) Inventors: Tsuneo Nakagawa, Komaki (JP); Takeshi Kurosaki, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/768,252

(22) Filed: Jan. 25, 2001

(65) Prior Publication Data

US 2001/0005777 A1 Jun. 28, 2001

(30) Foreign Application Priority Data

Aug. 4, 1998 (JP) .......................... 10-220156

(51) Int. Cl.$^7$ ............................... A61B 5/00
(52) U.S. Cl. ...................... 600/499; 606/202
(58) Field of Search ............... 600/499; 606/202

(56) References Cited

U.S. PATENT DOCUMENTS

| | | | | |
|---|---|---|---|---|
| 1,982,505 A | * | 11/1934 | Emerson | 606/202 |
| 3,120,846 A | * | 2/1964 | Fletcher | 600/499 |
| 4,033,337 A | * | 7/1977 | Raczkowski | 600/499 |
| 4,635,635 A | * | 1/1987 | Roninette-Lehman | 606/202 |
| 5,660,182 A | * | 8/1997 | Kuroshaki et al. | 600/499 |

* cited by examiner

*Primary Examiner*—Robert L. Nasser
(74) *Attorney, Agent, or Firm*—Oliff & Berridge, PLC

(57) ABSTRACT

An inflatable cuff for being wound and inflated around a body portion of a living subject to press the body portion in measuring a blood pressure of the subject, the cuff comprising: an inflatable bag; and an inner sheet member and an outer sheet member which are positioned inside and outside the inflatable bag, respectively, when the cuff is wound around the body portion of the subject; wherein at least a portion of the inner sheet member that is positioned inside the inflatable bag includes at least two layers which are separate from, and superposed on, each other.

5 Claims, 4 Drawing Sheets

INFLATABLE CUFF USED FOR BLOOD PRESSURE MEASUREMENT

This application is based on Japanese Patent Application No. 10-220156 filed Aug. 4, 1998, the contents of which are incorporated hereinto by reference.

BACKGROUND OF THE INVENTION

1. Field of the Invention

The present invention relates to an inflatable cuff which is cylindrically wound around a body portion of a living subject so as to press the body portion in measuring a blood pressure of the subject.

2. Discussion of Related Art

There is known an inflatable cuff which is cylindrically wound around a body portion of a living subject so as to press the body portion in measuring a blood pressure of the subject. The inflatable cuff includes a belt-like elongate bag which is formed of a nylon resin cloth, and a rubber-made inflatable bag accommodated in the belt-like elongate bag. Alternatively, the inflatable cuff includes a belt-like elongate bag which is formed by folding a vinyl resin sheet, and a portion of the elongate bag is high-frequency welded so as to define an air-tight inner space functioning as an inflatable bag.

In measuring a blood pressure of a patient, the inflatable cuff which is connected to a blood pressure (BP) measuring apparatus is wound around a body portion of the patient. The BP measuring apparatus increases the pressure of the inflatable cuff up to a target pressure value which is predetermined to be higher than a systolic blood pressure of the patient, subsequently slowly decreases the cuff pressure, and measures blood pressure values of the patient during the slow decreasing of the cuff pressure. Described in detail, the pressure oscillation produced in the inflatable bag of the cuff is detected as a pulse wave, and the systolic and diastolic blood pressure values of the patient are determined based on the change of respective amplitudes of successive heartbeat-synchronous pulses of the pulse wave. During the blood pressure measurement with the inflatable cuff being wound around the body portion of the patient, the patient undesirably suffers from subcutaneous bleeding in the skin of the body portion which is pressed by the inflatable cuff, due to strong friction locally caused between the inner surface of the inflatable cuff and the skin of the patient which is held in direct contact with the inner surface of the cuff. In particular, old-aged patients whose blood capillaries are weak tend to suffer from the problem.

SUMMARY OF THE INVENTION

It is therefore an object of the present invention to provide an inflatable cuff used for measuring a blood pressure of a living subject, which cuff prevents the skin of a body portion of the subject around which the cuff is wound, from suffering from subcutaneous bleeding.

As a result of an extensive study made by the inventors of the present invention, it has been found that the skin of the subject is locally pinched and corrugated by the inner sheet member of the cuff when the skin of the subject is pressed by the inflatable bag which has been inflated, due to large friction caused between the inner sheet member of the cuff which is positioned between the inflatable bag and the skin of the subject, and the skin of the subject which is held in direct contact with the inner sheet member. In this case, the skin of the subject is likely to suffer from the subcutaneous bleeding. The inventors have also found that the skin of the subject can be protected from suffering from the subcutaneous bleeding if the inflatable bag and the inner sheet member are easily slidable relative to each other.

The above object may be achieved according to a principle of the present invention, which provides an inflatable cuff for being wound and inflated around a body portion of a living subject to press the body portion in measuring a blood pressure of the subject, the cuff comprising: an inflatable bag; and an inner sheet member and an outer sheet member which are positioned inside and outside the inflatable bag, respectively, when the cuff is wound around the body portion of the subject; wherein at least a portion of the inner sheet member that is positioned inside the inflatable bag includes at least two layers which are separate from, and superposed on, each other.

In the present cuff wherein at least a portion of the inner sheet member that is positioned inside the inflatable bag is formed by at least two layers which are separate from, and superposed on, each other, one of the two layers which is adapted to be held in contact with the skin of the subject, and the other layer which is located on the side of the inflatable bag are permitted to be movable relative to each other in directions parallel to the two layers. Further, the above-indicated other layer which is located on the side of the inflatable bag can be formed by using a material which is easily slidable relative to the inflatable bag. Accordingly, the present arrangement is effective to prevent the skin of the subject from suffering from the subcutaneous bleeding which arises from strong friction between the cuff and the skin of the subject which is pressed by the cuff.

Preferably, the two layers of the inner sheet member are bonded to each other at respective peripheral portions thereof, so that a remaining portion of at least one of the two layers is movable relative to a remaining portion of the other layer in directions parallel to the two layers.

Preferably, the two layers comprise a bag-side layer which is located on the side of the inflatable bag, and a contact layer which is adapted to be held in close contact with the body portion of the living subject when the cuff is wound around the body portion, the bag-side layer being formed of a stretchable material. Preferably, the bag-side layer is formed of a material selected from the group consisting of a natural fiber woven fabric, a natural fiber unwoven fabric, a synthetic fiber woven fabric, and a synthetic fiber unwoven fabric, the contact layer being formed of a material selected from the group consisting of a long-fiber woven fabric and a long-fiber unwoven fabric. At least one of the natural fiber woven fabric and the natural fiber unwoven fabric preferably comprises at least one of a cotton fabric, a silk fabric, and a wool fabric. This arrangement permits easy sliding and easy displacement of the contact layer which is held in close contact with the skin of the subject and the bag-side layer which is located on the side of the inflatable bag, relative to each other, in directions parallel to the two layers.

BRIEF DESCRIPTION OF THE DRAWINGS

The above and other objects, features, advantages and technical and industrial significance of the present invention will be better understood by reading the following detailed description of a presently preferred embodiment of the invention, when considered in connection with the accompanying drawings, in which.

DETAILED DESCRIPTION OF PREFERRED EMBODIMENT

Figure 1:
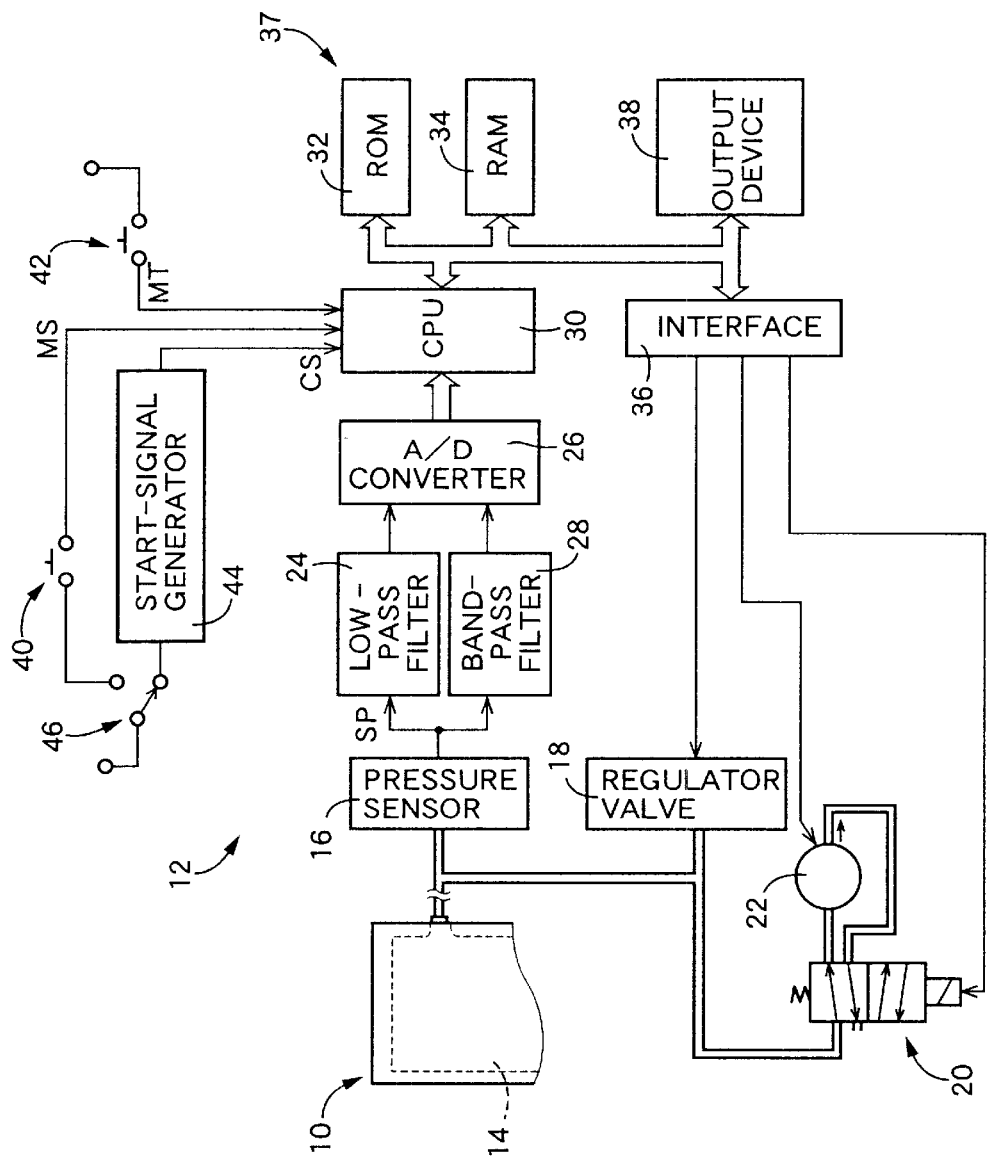
FIG. 1 is a diagrammatic view of a blood pressure measuring apparatus which includes an inflatable cuff constructed according to one embodiment of the present invention.

Referring first to FIG. 1, there is schematically shown a blood pressure (BP) measuring apparatus 12 which includes an inflatable cuff 10 constructed according to one embodiment of the present invention. The inflatable cuff 10 includes an inflatable bag 14 connected to a pressure sensor 16 and a pressure regulator valve 18, and an air pump 22 via a selector valve 20. The pressure sensor 16 detects an air pressure in the inflatable bag 14, and generates a pressure signal SP indicative of the detected pressure. The regulator valve 18 functions as a pressing-force changing device which changes a pressing force of the cuff applied to the body portion of the subject. The regulator valve 18 is adapted to slowly or quickly deflate the inflatable bag 14 by changing a cross sectional area of an air passage thereof. The selector valve 20 is a solenoid-operated valve, and is selectively placed in an air-supplying position and an air-discharging position. In the air-supplying position, the selector valve 20 permits the inflatable bag 14 of the cuff 10 to communicate with an outlet of the air pump 22 and permits an inlet of the air pump 22 to communicate with the atmosphere. In the air-discharging position, the control valve 20 permits the inflatable bag 14 of the cuff 10 to communicate with the inlet of the air pump 22 and permits the outlet of the air pump 22 to the atmosphere. The selector valve 20 functions as a cuff deflating device. The air pump 22 generates, a vacuum whose pressure is lower than a pressure of the ambient atmosphere, i.e., atmospheric pressure, at the inlet thereof, and functions as a vacuum or a negative-pressure producing device.

The pressure signal SP is supplied to a low-pass filter 24 and a band-pass filter 28. The low-pass filter 24 permits only a static component of the pressure signal SP to pass therethrough, for thereby providing a cuff-pressure signal SK indicative of the air pressure of the cuff 10. The cuff-pressure signal SK is supplied to a central processing unit (CPU) 30 via an analog to digital (A/D) converter 26. The band-pass filter 28 permits only an oscillation component of the pressure signal SP to pass therethrough, for thereby providing a pulse wave signal SM indicative of a pressure oscillation produced in the cuff 10 in synchronism with heartbeat of the subject. The pulse wave signal SM is also supplied to the CPU 30 via the A/D converter 26.

The CPU 30 cooperates with a read only memory (ROM) 32, a random access memory (RAM) 34, and an interface 36 to constitute an arithmetic control device 37 which serves as blood pressure (BP) determining means. The CPU 30 processes input signals according to control programs pre-stored in the ROM 32 by utilizing a temporary-storage function of the RAM 34. The CPU 30 operates an output device 38 to display BP values of the subject, and controls the regulator valve 18, selector valve 20, and air pump 22.

The CPU 30 receives a first START signal MS from a START switch 40, a STOP signal MT from a STOP switch 42, and a second START signal CS from a START signal generator 44. A MANUAL/AUTO selector switch 46 is operable for selectively connecting one of the START switch 40 and the START signal generator 44 to the CPU 30. The START signal generator 44 includes a well-known flip-flop circuit, for example, and repeatedly generates the second START signal CS at a period pre-set through a period-setting device not shown.

Figure 2:
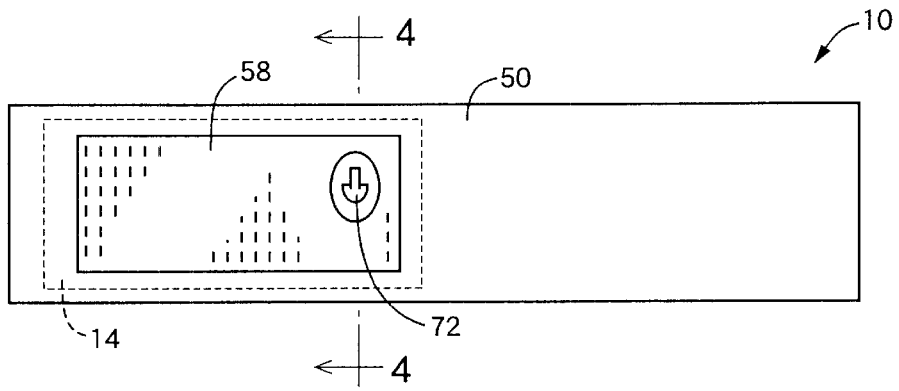
FIG. 2 is a plan view of an outer surface of the cuff of FIG. 1.
Figure 3:
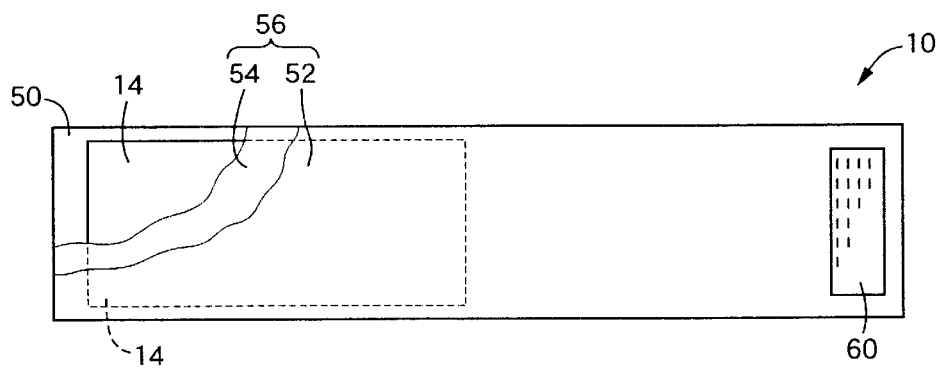
FIG. 3 is a plan view of an inner surface of the cuff of FIG. 1
Figure 4:
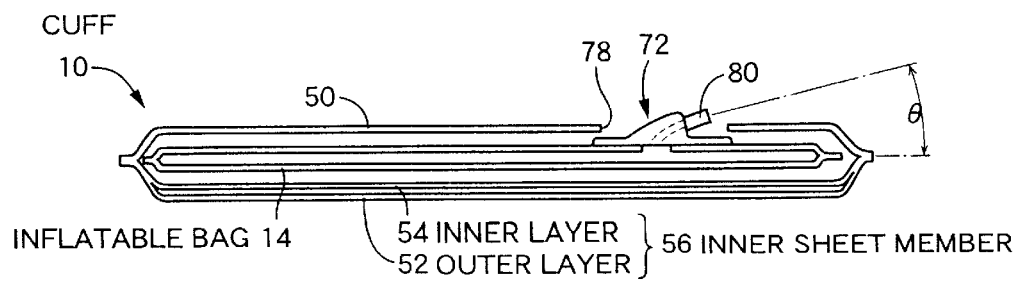
FIG. 4 is a transverse-cross sectional view of the cuff of FIG. 1 taken along line 4—4 of FIG. 2.

Referring next to FIGS. 2–4, there is shown the inflatable cuff 10 according to the present invention. FIGS. 2 and 3 show an outer major surface and an inner major surface of the cuff 10, respectively, while FIG. 4 shows a transverse cross-sectional view of the cuff 10 taken along line 4—4 of FIG. 2. As shown in FIGS. 2–4, the inflatable cuff 10 has an elongate bag-like configuration formed by an outer sheet member 50 and an inner sheet member 56 which are bonded together at their peripheral portions by a high-frequency welding technique, for example. The outer sheet member 50 is a belt-like sheet member which is formed of a synthetic resin that is reinforced by fibers extending in a longitudinal and a lateral directions thereof, and which is flexible while it is less likely to be stretchable. The inner sheet member 56 consists of an outer layer 52 (contact layer) which is to be held in contact with the skin of the body portion of the subject when the cuff 10 is wound around the body portion, and an inner layer 54 (bag-side layer) which is located on the side of the inflatable bag 14. The outer and inner layers 52, 54 are separate from, and superposed on, each other. The outer layer 52 is formed of a nonwoven fabric which has relatively long fibers and which is reinforced or lined with a synthetic-resin layer. The inner layer 54 is formed of a relatively thin woven or nonwoven fabric made of a natural fiber such as a cotton cloth suitable for use in a cast bandage, a silk fabric, or a wool fabric. The inner layer 54 may be formed of a relatively thin woven or nonwoven fabric made of a synthetic fiber. For enhancing the touch of the cuff 10 as felt by the living subject when the cuff 10 is wound around the skin of the body portion of the subject, the inner major surface of the cuff 10 which is held in direct contact with the skin of the subject is provided by one of the opposite surfaces of the outer layer 52, which surface is not lined with the synthetic-resin layer. The exposed surface of the outer layer 52 formed of the long fibers is raised or gigged.

The inflatable bag 14 is accommodated in the elongate bag formed by the outer and inner sheet members 50, 56 described above, such that the inflatable bag 14 is located at one of longitudinally opposite end portions of the cuff 10, which end portion is not exposed or visible, and is held in direct contact with the skin of the body portion of the subject when the cuff 10 is cylindrically wound around the body portion. The inflatable bag 14 has a rectangular configuration having a width dimension which is slightly smaller than that of the cuff 10, and a length dimension which is about half of that of the cuff 10. The inflatable bag 14 is formed by two vinyl chloride sheets whose peripheral portions are bonded to each other by high-frequency welding, so that the inflatable bag 14 is air-tightly closed.

Figure 5:
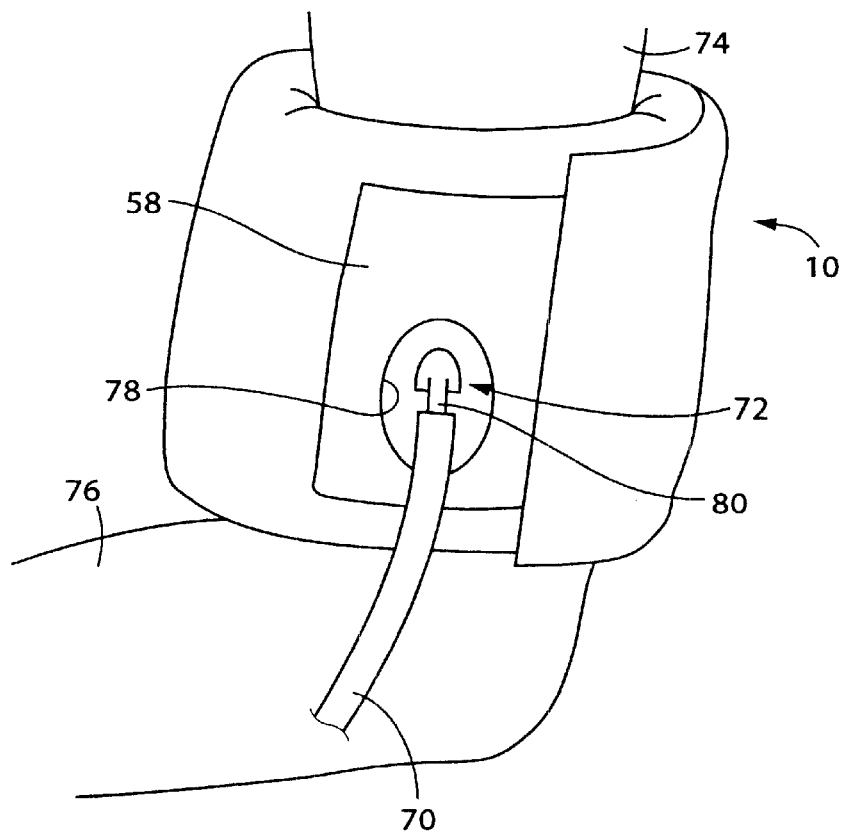
FIG. 5 is a view showing the cuff shown in FIGS. 2–4 which is wound around a body portion of a living subject.

A pair of fastener pads 58, 60, each of which is formed of an adhesive sheet having self-adhesiveness, are provided respectively on the outer surface of the cuff 10 provided by the outer sheet member 50 at one of the longitudinally opposite end portions of the cuff 10, which end portion corresponds to the inflatable bag 14, and the inner surface of the cuff 10 provided by the inner sheet member 56 at the other longitudinal end portion which is remote from the inflatable bag 14. As shown in FIG. 5, the cuff 10 is cylindrically wound around the body portion of the subject, e.g., an upper arm 74, such that the longitudinal end portion which is remote from the inflatable bag 14 is superposed on the longitudinal end portion which corresponds to the inflatable bag 14, with the fastener pads 58, 60 being bonded to each other.

Figure 6:
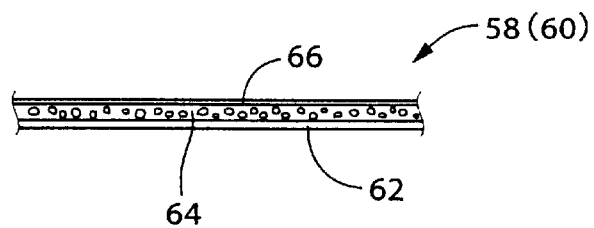
FIG. 6 is a cross-sectional view showing a structure of a fastener pad used in the cuff of FIG. 1.

The fastener pads 58, 60 are disengageably held in engagement with each other when the cuff 10 is wound around the upper arm, for example. The adhesive sheet of each of the fastener pads 58, 60 has a three-layer structure, as shown in FIG. 6, consisting of a flexible sheet base layer 62, a foamed layer 64 which is formed on the sheet base layer 62 by using a soft synthetic resin and which has a closed cell structure, and an adhesive layer 66 formed on the foamed layer 64. The sheet base layer 64 is formed of a kraft paper, PE oriented film, PE cross laminate film, or aluminum-deposited PET film, for instance. The foamed layer 64 is formed of a polypropylene resin having a thickness value of about 0.5~2.0 mm. The adhesive layer 66 is formed by coating the upper surface of the foamed layer 64 with a self-adhesive agent which is obtained, for instance, by mixing a rubber with a softening agent such as a pine tar, or a mineral oil. The self-adhesive agent exhibits a suitable adhesive strength with respect to a material similar to the self-adhesive agent, but exhibits substantially no adhesive strength with respect to other materials.

The inflatable bag 14 is provided with a connector 72 for connecting the inflatable bag 14 to an air pipe 70 formed of an elastic material, through which a pressurized air is supplied from the air pump 22. The connector 72 is located at an intermediate position in a width direction of the inflatable bag 14, such that the connector 72 is distant, by a suitable distance, from a distal end of the cuff 10, which distal end of the cuff 10 is located on the side of a forearm 76 (FIG. 5) when the cuff 10 is wound around the upper arm 74. The position of the connector 72 corresponds to an intermediate portion of the cuff 10 in a width direction thereof, and is determined so that the air pipe 70 connected to the connector 72 is not bent when the cuff 10 is wound around the upper arm 74 with the distal end of the cuff 10 being held in contact with the inner portion of the forearm 76.

Like the air pipe 70, the connector 72 is a relatively soft elastic member in the form of a natural or synthetic rubber sheet, for instance, and is fixed to the inflatable bag 14 by bonding using an adhesive agent, thermocompression bonding, or molding. The position of the inflatable cuff 14 to which the connector 72 is attached is located, in the lengthwise direction of the cuff 10, at a position where the connector 72 is externally exposed in a state in which the cuff 10 is wound around the body portion of the subject such that the two longitudinally opposite end portions of the cuff 10 are superposed on each other with the pair of fastener pads 68, 60 being bonded to each other. The outer sheet member 50 of the cuff 10 is formed with an elliptical hole 78 at a position corresponding to the connector 72. The connector 72 is exposed to the outer surface of the cuff 10 through the hole 78.

The connector 62 includes a conduit 80 to which the air pipe 70 is connected for communication with the inflatable bag 14. The conduit 80 is formed integrally with the connector 62 165 such that the conduit 80 outwardly projects from the inflatable bag 14 by an angle θ which falls in a range of from 20 degrees to 40 degrees with respect to the widthwise direction of the cuff 10 in a plane which is perpendicular to a plane of the cuff 10 and is parallel to the widthwise direction thereof. The conduit 80 is an elastic member similar to the connector 72.

The material and the structure of the present cuff 10 constructed as described above are determined such that the cost of the cuff 10 is made as low as possible while assuring a high degree of operating reliability in pressing the body portion of the living subject during the blood pressure measurement, so that the cuff 10 can be used as a so-called disposable cuff exclusively used for a specific patient for the purpose of preventing the nosocominal infection.

There will be described a significance and a function of the inner layer 54 of the inner sheet member 56. When the conventional cuff is wound around the body portion of the patient in measuring the blood pressure, the subcutaneous bleeding tends to occur in the skin of the subject due to strong friction between the cuff and the skin of the subject which is pressed by the cuff 10. Since the inner layer 54 of the inner sheet member 56 of the present cuff 10 is located on the side of the inflatable bag 14 and is formed of a relatively thin nonwoven or woven fabric made of the synthetic or natural resin, the inner layer 54 is likely to be slidable relative to the inflatable bag 14 formed of the vinyl chloride owing to a low friction coefficient therebetween. Moreover, the inner layer 54 which is separate from, and superposed on, the outer layer 52 is movable relative to the outer layer 52 to a some extent in directions parallel to the two layers. Accordingly, the present arrangement permits a relative movement of the inflatable bag 14 and the skin of the subject which is held in close contact with the outer layer 52 when the body portion of the subject is pressed by the cuff 10, for thereby preventing the skin of the subject from suffering from the subcutaneous bleeding.

Figure 7:
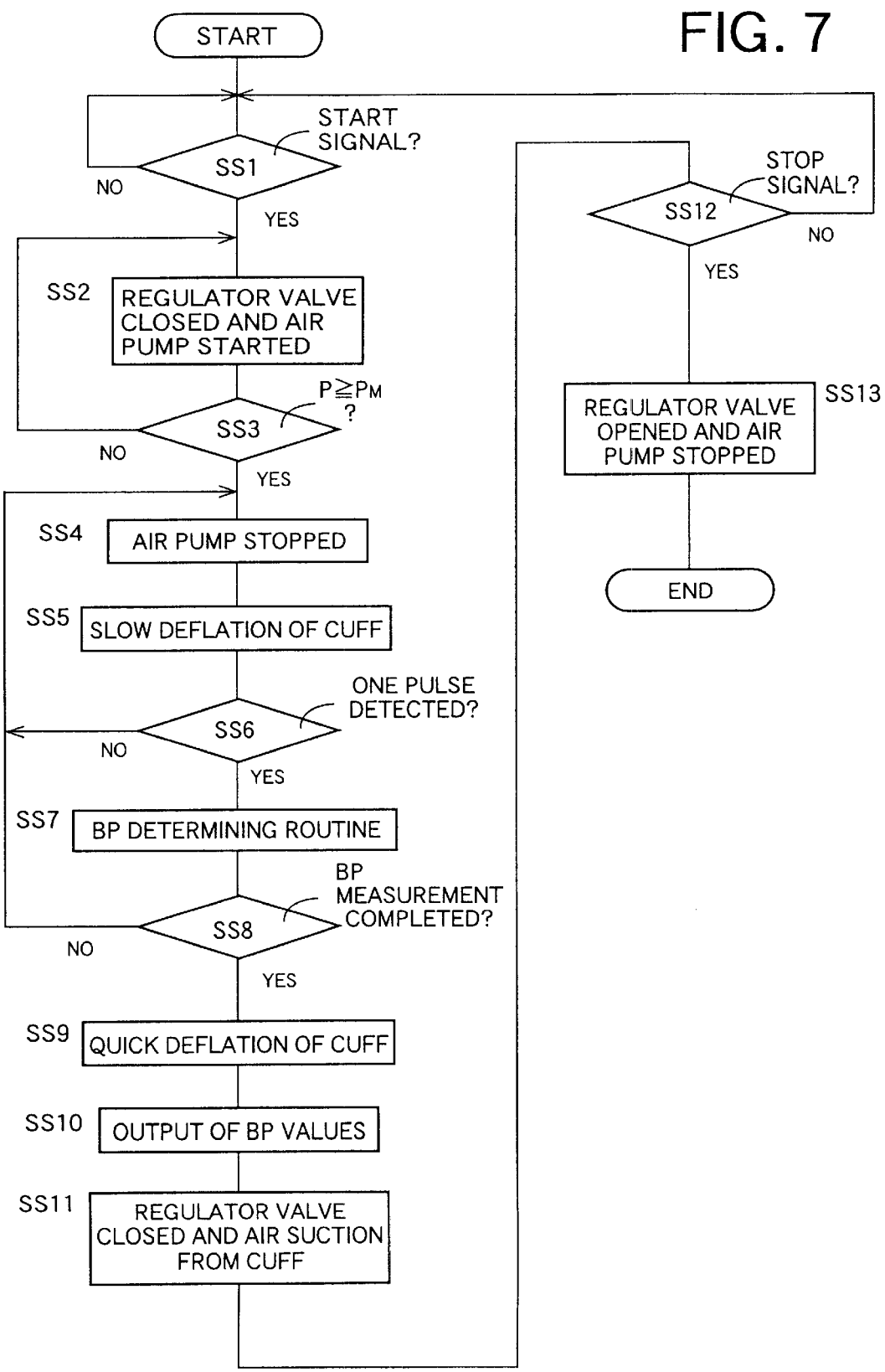
FIG. 7 is a flow chart illustrating a control program according to which the apparatus of FIG. 1 operates.

FIG. 7 shows a flow chart representing a control program which is carried out by the arithmetic control device 37. The control program is initiated with Step SS1 in which the CPU 30 judges whether the first or second START signal MS or CS is present at the CPU 30. If an affirmative judgment is made at step SS1, the control flow goes to Step SS2 to close the pressure regulator valve 18, place the selector valve 20 in the air-supplying position, and operate the air pump 22 so as to start inflation of the cuff 10, i.e., start increasing an air pressure P in the cuff 10. Step SS2 is followed by Step SS3 to judge whether the cuff pressure P has reached a predetermined reference value PM. If a negative judgment is made in Step SS3, the CPU 30 repeats Steps SS2 and SS3. If an affirmative judgment is made in Step SS3, the control flow goes to Step SS4 to stop the air pump 22 and subsequently to Step SS5 to open the regulator valve 18 so as to start slow deflation of the cuff 10, i.e., start decreasing the cuff pressure P at a predetermined rate, e.g., about 2 to 3 mm/Hgsec.

Step SS5 is followed by Step SS6 to judge whether or not one pulse of the pulse wave signal SM corresponding to one heartbeat of the subject has been supplied form the cuff 10. If a negative judgment is made in Step SS6, Steps SS4 through SS6 are repeated. If an affirmative judgment is made in Step SS6, the control of the CPU 30 goes to Step SS7 to execute a blood pressure value determining routine. In this routine, the CPU 30 determines a cuff pressure P when the respective pulse amplitudes of the pulse wave signal SM have significantly largely increased, as a systolic blood pressure of the subject; determines a cuff pressure P when the pulse amplitudes have become maximum, as a mean blood pressure of the subject; and determines a cuff pressure P when the pulse amplitudes have significantly largely decreased, as a diastolic blood pressure of the subject. In the following Step SS8, the CPU 30 judges whether the blood pressure measurement in Step SS7 has been completed.

If a negative judgment is made in Step SS8, Steps SS4 through SS8 are repeated. If an affirmative judgment is made in Step SS8, the control flow goes to Step SS9 to open the regulator valve 18 so as to quickly deflate the cuff 10 in a predetermined time period. Step SS9 is followed by Step SS10 to operate the display device 38 to indicate the measured blood pressure values. Subsequently, Step SS11 is implemented to close regulator valve 18, place the selector valve 20 in the air-discharging position, and operate the air pump 20 for a predetermined time period. Thus, the air remaining in the inflatable bag 14 is forcibly discharged therefrom to produce a vacuum or a negative pressure therein. Step SS11 is followed by Step SS12 to judge whether the STOP signal MT is present at the CPU 30. If a negative judgment is made in Step SS12, Steps SS1 through SS 12 are repeatedly implemented. If an affirmative judgment is made in Step SS12, the control flow goes to Step SS13 to stop the air pump 22 and open the regulator valve 18.

The BP measuring apparatus 12 executes Step SS11 to produce a vacuum in the inflatable bag 14 of the cuff 10 during a non-BP measurement period following a BP measurement carried out in response to a manual operation of the START switch 40 or a periodic generation of a START signal from the signal generator 44. Since the inlet of the air pump 22 and the inflatable bag 14 are held in communication with each other through the selector valve 20, the air is discharged from the inflatable bag 14, and the cuff 10 is deflated, i.e., the thickness of the inflatable bag 14 is reduced during the non-BP measurement period. Accordingly, the area of contact of the cuff 10 with the skin of the patient's arm around which the cuff is wound, is minimized, so that air is permitted to more easily flow between the cuff and the patient's skin, thereby preventing the skin from becoming sweaty or stuffy.

While the present invention has been described in its presently preferred embodiment, the invention may otherwise be embodied.

In the illustrated embodiment, the inner sheet member 56 has a two-layer structure consisting of the outer layer 52 and the inner layer 54 which are separate from, and superposed on, each other. The inner sheet member 56 may be constituted by three or more layers.

The fastener pads 58, 60 of the cuff 10 of the illustrated embodiment are provided by the respective adhesive sheets which are bonded together when the cuff 10 is wound around the body portion of the subject. The fastener pads 58, 60 may have a multiplicity of looped fibers, and a multiplicity of elastically deformable hooks made of a synthetic resin, respectively, which looped fibers and hooks are formed on the respective outer surfaces of the fastener pads 58, 60, so that the looped fibers and the hooks are disengageably or detachably held in engagement with each other, for thereby permitting the cuff which is wound around the body portion of the subject to be securely fixed relative to the body portion.

In the illustrated embodiment, the air pipe 70 is connected to the connector 72 provided at an intermediate portion of the cuff 10 in the widthwise direction thereof. The air pipe 70 may be connected to a connector which is attached to the distal end of the cuff 10.

While the cuff 10 of the illustrated embodiment is a straight elongate member, the cuff 10 may be a curved elongate member as a whole.

While the outer sheet member 50, and the outer and inner layers 52, 54 of the inner sheet member 56 are formed of the respective materials which permit the cuff 10 to be used as a disposable cuff, the materials of the outer sheet member 50, and the outer and inner layers 52, 54 of the inner sheet member 56 are not limited to those of the illustrated embodiment.

It is to be understood that the present invention may be embodied with various other changes, modifications and improvements, which may occur to those skilled in the art, without departing from the spirit and scope of the invention defined in the following claims.

What is claimed is:

1. An inflatable cuff for being wound and inflated around a body portion of a living subject to press said body portion in measuring a blood pressure of the subject, the cuff comprising:

an inflatable bag; and an inner sheet member and an outer sheet member which are positioned inside and outside said inflatable bag, respectively, when the cuff is wound around said body portion of the subject;

wherein at least a portion of said inner sheet member that is positioned inside said inflatable bag includes at least two layers which are separate from, and superposed on, each other;

wherein said at least two layers of said inner sheet member are bonded to each other at respective peripheral portions thereof, so that a remaining portion of at least one of said at least two layers is slidable relative to a remaining portion of the other of said at least two layers;

wherein said two layers comprise a bag-side layer which is located on the side of said inflatable bag, and a contact layer which is adapted to be held in close contact with said body portion of the living subject when the cuff is wound around said body portion, said bag-side layer being formed of a stretchable material; and wherein said contact layer comprises a fabric layer and a synthetic-resin layer, said fabric layer having opposite surfaces, one of which is located on the side of said bag-side layer and lined with said synthetic-resin layer, so that said bag-side layer is slidable relative to said contact layer.

2. An inflatable cuff according to claim 1, wherein said bag-side layer is formed of a material selected from the group consisting of a natural fiber woven fabric, a natural fiber unwoven fabric, a synthetic fiber woven fabric, and a synthetic fiber unwoven fabric, said contact layer being formed of a material selected from the group consisting of a long-fiber woven fabric and a long-fiber unwoven fabric.

3. An inflatable cuff according to claim 1, wherein at least one of said natural fiber woven fabric and said natural fiber unwoven fabric comprises at least one of a cotton fabric, a silk fabric, and a wool fabric.

4. An inflatable cuff according to claim 1, further comprising a connector to which a gas-supply pipe is connected for supplying a pressurized gas to said inflatable bag.

5. An inflatable cuff according to claim 4, wherein said connector is located at an intermediate position of the cuff in a width direction therefore, such that said connector is distant, by a suitable distance, from a distal end of the cuff.

* * * * *